United States Patent
Wang et al.

(10) Patent No.: US 6,863,123 B2
(45) Date of Patent: Mar. 8, 2005

(54) FLEXIBLE AND MOBILE HIGH TRANSITION RATE OF TEMPERATURE TEST DEVICES

(75) Inventors: Jeng-Yau Wang, Taoyuan Hsien (TW); Ruey-Shyong Song, Hsinchu Hsien (TW)

(73) Assignee: Chung-Shan Institute of Science and Technology, Taoyuan Hsien (TW)

( * ) Notice: Subject to any disclaimer, the term of this patent is extended or adjusted under 35 U.S.C. 154(b) by 203 days.

(21) Appl. No.: 10/262,878

(22) Filed: Oct. 3, 2002

(65) Prior Publication Data

US 2003/0066639 A1 Apr. 10, 2003

(30) Foreign Application Priority Data

Oct. 9, 2001 (TW) ...................................... 90217202 U

(51) Int. Cl.⁷ ........................... F25B 29/00; G01M 7/00
(52) U.S. Cl. ...................... 165/263; 165/264; 165/48.1; 165/61; 165/64; 73/865.6; 73/663; 324/760; 374/57; 62/78
(58) Field of Search ........................... 165/61, 64, 263, 165/264, 48.1; 73/865.6, 663; 62/78; 324/760; 374/57

(56) References Cited

U.S. PATENT DOCUMENTS

| | | | | |
|---|---|---|---|---|
| 2,345,204 A | * | 3/1944 | Lodwig | |
| 3,049,913 A | * | 8/1962 | Hunt | |
| 3,142,172 A | * | 7/1964 | Taccogna | |
| 3,241,358 A | * | 3/1966 | Booth et al. | |
| 3,664,181 A | * | 5/1972 | Conrad et al. | |
| 4,092,869 A | * | 6/1978 | Kimball | |
| 4,739,622 A | * | 4/1988 | Smith | 62/78 |
| RE32,933 E | * | 5/1989 | Vander Schaaf | 165/61 |
| 5,450,018 A | * | 9/1995 | Rieser et al. | 324/760 |
| 5,513,538 A | * | 5/1996 | Baker et al. | 73/865.6 |
| 5,613,776 A | * | 3/1997 | Turner et al. | 165/61 |
| 5,675,098 A | * | 10/1997 | Hobbs | 73/865.6 |
| 6,271,024 B1 | * | 8/2001 | Sve et al. | |
| 6,332,325 B1 | * | 12/2001 | Monfort | 62/78 |
| 6,446,508 B1 | * | 9/2002 | Peterson et al. | 73/875 |
| 6,640,555 B2 | * | 11/2003 | Cashin | 62/50.2 |
| 6,711,961 B2 | * | 3/2004 | Theriault et al. | 324/760 |

FOREIGN PATENT DOCUMENTS

| | | | |
|---|---|---|---|
| DE | 10236058 | * | 7/2003 |
| SU | 1675717 | * | 9/1991 |

* cited by examiner

*Primary Examiner*—John K. Ford
(74) *Attorney, Agent, or Firm*—Leong C. Lei

(57) ABSTRACT

A high thermal change rate of test apparatus aims to realize test equipment requirement of highly accelerated life test (HALT) and highly accelerated stress screening(HASS). Structurally, the apparatus is provided with a cabinet body with an interior for placing test specimen. The cabinet body is provided with elements of fans, electric heating tubes and liquid nitrogen nozzles therein. The positions of the cabinet body and the control system are separate. Several groups (normally 2 or 3 groups, depends on the size of cabinet) of liquid nitrogen pipes connecting the cabinet body are flexible stainless steel pipes for enclosing and insulating sleeve tubes. During full-speed temperature cooling, all groups of the pipes simultaneously eject liquid nitrogen. When temperature is constant, only one group of liquid nitrogen pipe with cryogenic valve and nozzles is used and micro-adjusted to achieve good temperature stability. The cabinet body can match different types of shaker combinations to perform temperature/vibration test with high transition rate of temperature, and be used as a single high thermal change rate of temperature cabinet, can have relatively great assembly flexibility in response to test requirement. The entire apparatus has higher mobility and flexibility than conventional temperature/vibration cabinets.

10 Claims, 10 Drawing Sheets

FLEXIBLE AND MOBILE HIGH TRANSITION RATE OF TEMPERATURE TEST DEVICES

BACKGROUND OF THE INVENTION (a) Field of the Invention

This invention relates to a high thermal change rate test device, and more particularly to the following: (1) In response to test form requirements, mobility is high, there is great of flexibility shakers, and more usage. (2). Liquid nitrogen enters the chamber via multiple pipes. Electric heaters are also divided into two groups for control, and to achieve the effects of a rapid rise and fall of temperature, and constant temperature stability. (3). The dispersion effect of spray ejected from liquid nitrogen nozzles is good, and it has a good temperature reduction efficiency and temperature distributing effect when used in the temperature cabinet. (4). Suitable pressure of liquid nitrogen pipes can be adjusted to satisfy cooling rate requirements, and prevent excessive pressure to cryogenic valves lead to loss of control and cause excessively low temperature.

(b) Description of the Prior Art

In a conventional temperature test apparatus for conducting Highly Accelerated Life Test (HALT) or Highly Accelerated Stress Screening (HASS) of electronic hardware, the form of assembly and the matching shaker are almost fixed. The mobility and form of test assembly has little flexibility. The precision of temperature control of liquid nitrogen used is not satisfactory. In addition if achieving a high temperature change rate for a conventional compressor refrigerating system is required, the cost is high, the mobility and assembly flexibility are low, the rate of breakdown after long-term use is high, and maintenance is not easy.

SUMMARY OF THE INVENTION

The object of this invention is to provide a high temperature change rate test device that can quickly be set up with any kind of shaker. Structurally, the device is provided with a cabinet body with an interior for placing test samples. The cabinet body includes the elements of fans, electric heaters, liquid nitrogen pipes and nozzles therein. Cryogenic valves should be put as near the nozzles as possible to get a better control. The cryogenic valves are fixed on the outer wall of the cabinet. Temperature sensors are movably disposed in the test space. The cabinet body and control system are separate, the power cords, control wires, and temperature sensors are interconnected by connectors to enable the cabinet body to be moved. Liquid nitrogen pipes connecting the cabinet body are also flexible interconnecting hoses. To achieve temperature stability when temperature is constant, the controller itself adjusts a suitable control parameter (e.g. P.I.D parameter), and cooperates with electric heaters capable of suitable power micro-adjustment and liquid nitrogen pipes. The liquid nitrogen pipes are multiple in number and can simultaneously eject liquid nitrogen during full-speed temperature reduction. When temperature is constant, only one group of the liquid nitrogen pipes is used and micro-adjusted. Pressures valves and pressure meters are mounted in front of cryogenic valves of liquid nitrogen pipes to adjust suitable pressure so adequate liquid nitrogen can flow into the cabinet to achieve the required temperature reduction rate, without exceeding the pressure tolerable by the cryogenic valves. Heating is also divided into full-heating and micro-adjustment, achieving quick increase of temperature and temperature stability.

Another object of the invention is to provide a high cooling rate of temperature test apparatus that has a good liquid nitrogen spray dispersion effect during temperature reduction and that prevents ejection of liquid jets or drops direction on the test space, preventing partial uneven cold temperature distribution. Structurally, the outlet of the nozzle is provided with a flared tube sleeve. The nozzle and the flared tube sleeve are connected by solder points to form multiple small holes between the nozzle and the flared tube sleeve so that liquid nitrogen ejects widely spray without liquid drops. The spraying effect is satisfactory after numerous experiments. The nozzles can easily be made by the user and are low in cost.

A further object of the invention is to provide a high temperature transition rate test apparatus which has assembly flexibility and mobility in response to test form requirements. Structurally, the cabinet body covers a baseplate of low heat conductivity and is easy to assemble (e.g. bakelite carbolite). The baseplate can be with or without an opening depending on the test form. In the case of a baseplate without an opening, temperature tests can be conducted independently. In the case of a baseplate with an opening, a temperature/vibration test can be conducted.

The foregoing object and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

BRIEF DESCRIPTION OF THE DRAWINGS

The foregoing and other features and advantages of the present invention will be more clearly understood from the following detailed description and the accompanying drawings, in which.

DETAILED DESCRIPTION OF THE PREFERRED EMBODIMENT

The following descriptions are of exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
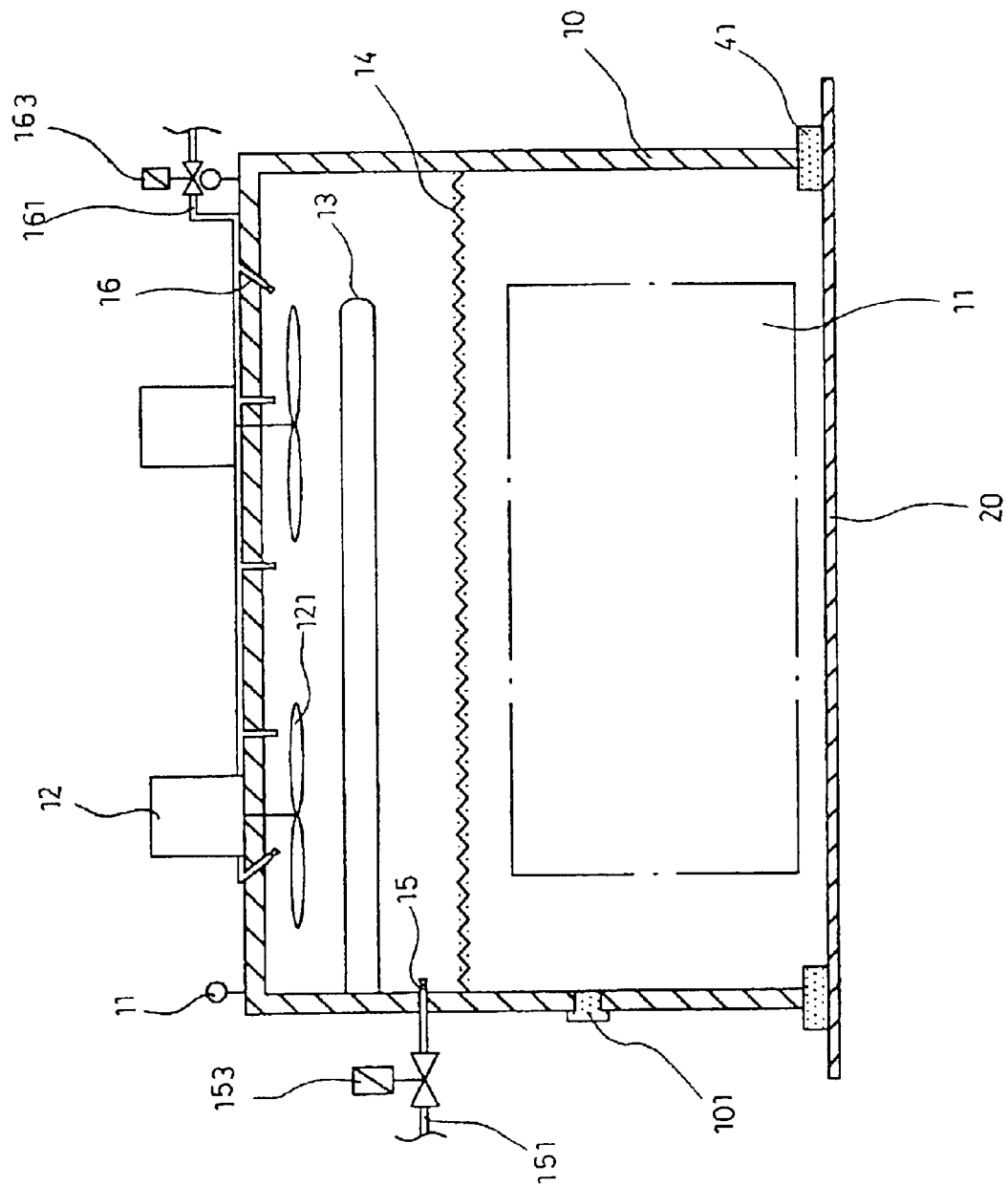
FIG. 1 is a schematic view of a cabinet body of this invention, which is shown to match a baseplate without an opening for use as a conventional temperature cabinet.
Figure 2:
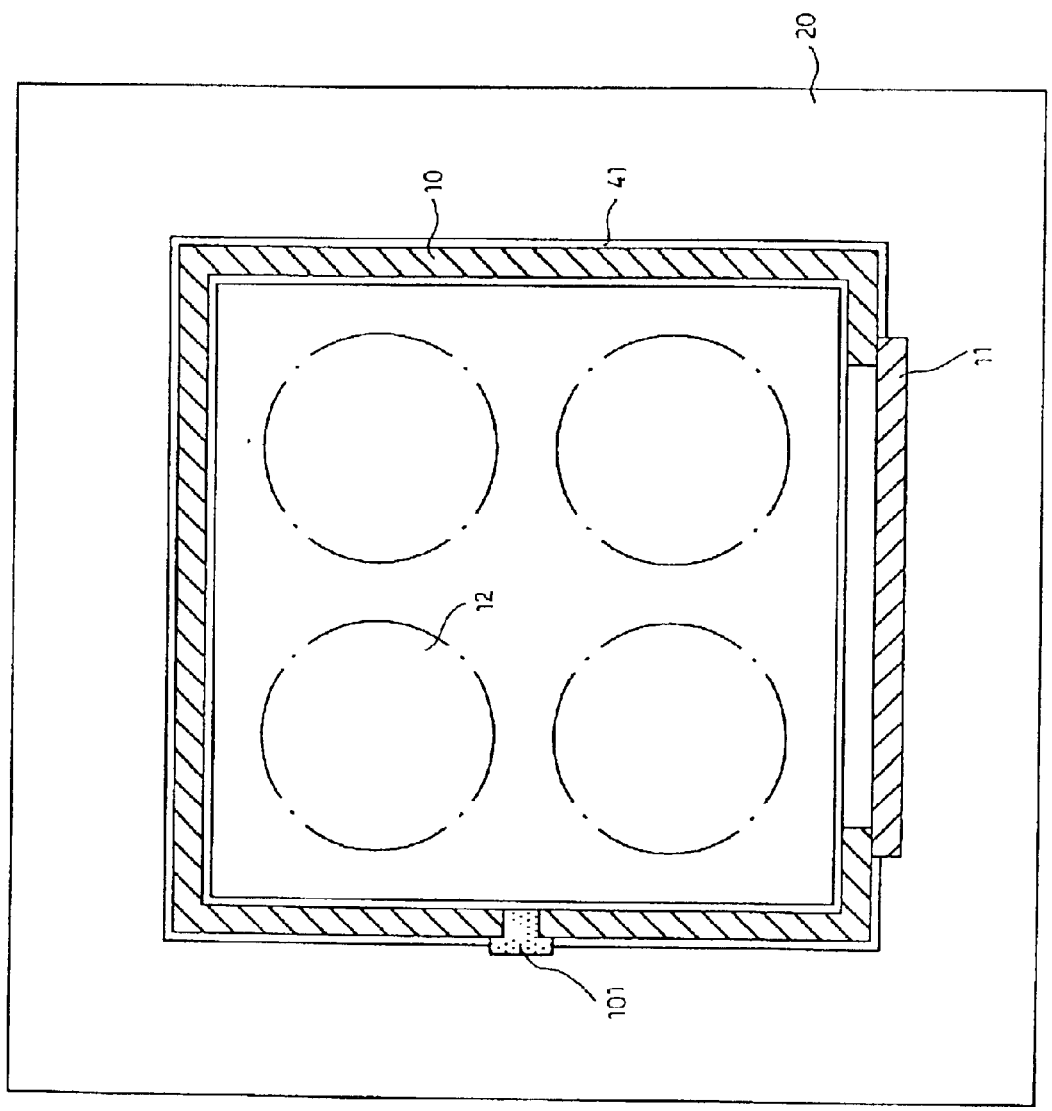
FIG. 2 is a bottom schematic view of the cabinet body and a bakelite (carbolite) baseplate (merely showing the relationship between the cabinet body and the bakelite baseplate)
Figure 3:
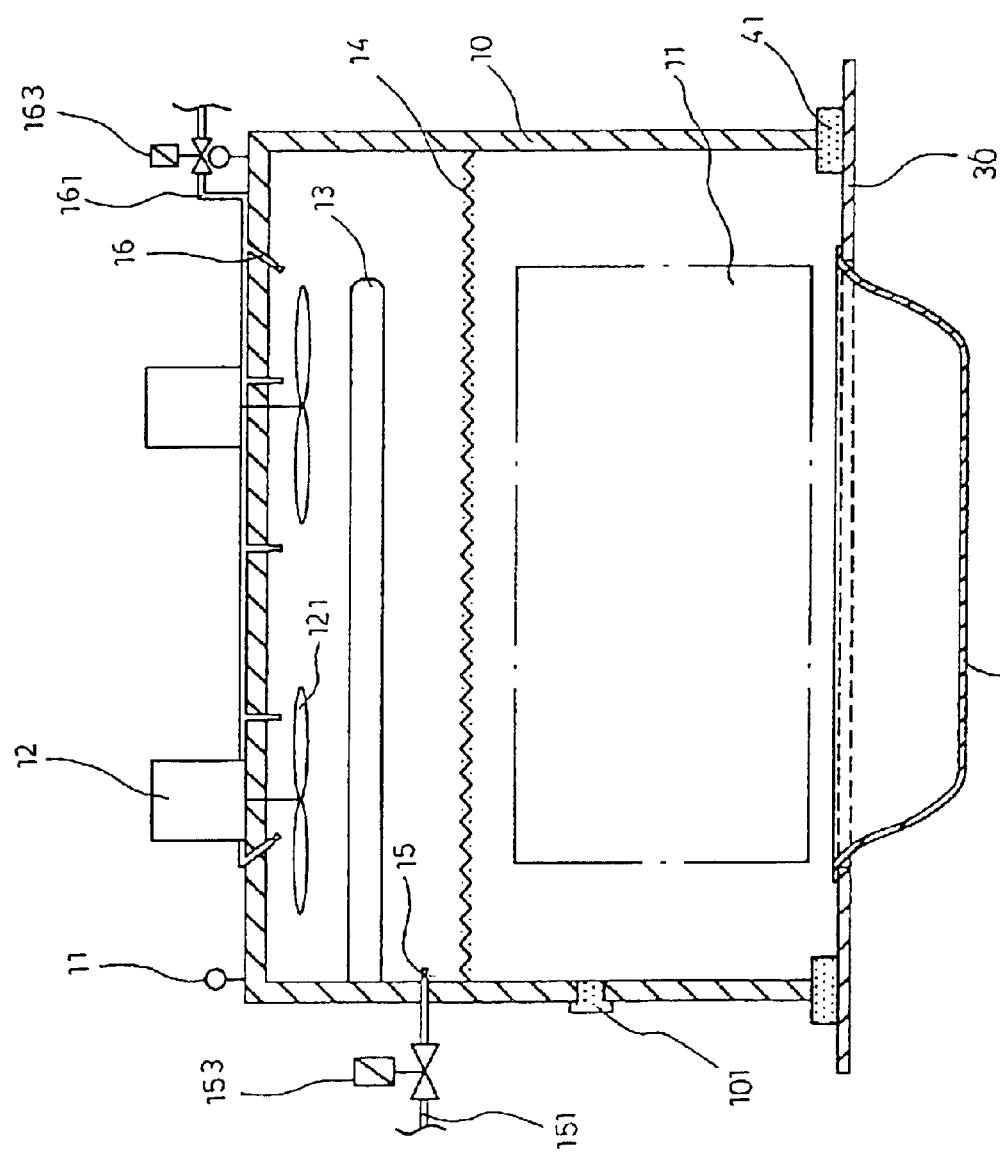
FIG. 3 is a front schematic view of the cabinet body placed on the bakelite baseplate with opening and a heat-resistant thin soft rubber.
Figure 4:
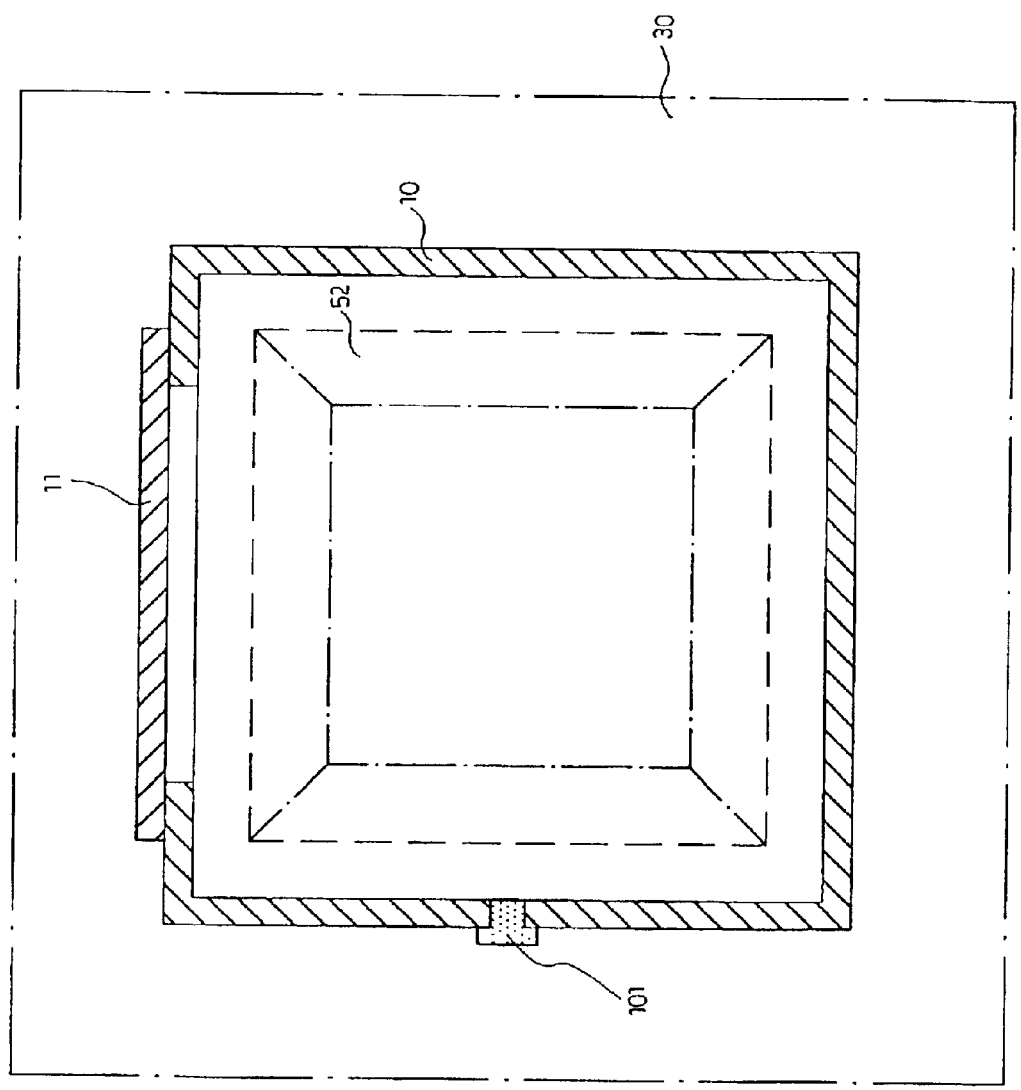
FIG. 4 is an elevation schematic view of FIG. 3, showing the cabinet body matching the bakelite baseplate with opening and the heat-resistant thin soft rubber.

Referring to FIGS. 1 and 2, this invention structurally is provided with a cabinet body 10 with five sides made from heat insulating cabinet walls (e.g., inner and outer layers of the cabinet wall are SUS#304 stainless steel; laminate layers are glass fiber) so that test samples (such as electronic hardware) can be placed in its interior for conducting high thermal rate tests. The cabinet body 10 itself is not provided with a bottom wall so as to match a bakelite baseplate 20 not provided with an opening or match a bakelite baseplate 30 with an opening. In the case of bakelite baseplate 30 with an opening (see FIGS. 3 and 4), temperature/vibration tests can be carried out. To perform a temperature vibration test, before the cabinet body is put in place, the user has more space to first lock the test sample with the matching bakelite baseplate with the opening on the shaker via a heat-resistant thin soft rubber. The corners of cabinet body 10 are provided with lugs 11 to facilitate lifting and placement of cabinet body 10. One side of the cabinet body 10 is provided with a cabinet door 11 which can be opened from the left or right, and through which test specimens can be adjusted and functional test set up. Test specimen functional test cables pass through a test hole 101 formed in one side of the cabinet body 10 to conduct a functional test. The interior of the cabinet body 10 is provided with a plurality of high speed electric heating tubes 13 and a stainless steel mesh 14. Inner side wall surfaces and upper side inner wall surfaces of the cabinet body 10 are provided with a plurality of nozzles 15, 16, These nozzles 15, 16 are connected to liquid nitrogen pipes so that nozzles 15, 16 can widely eject mist-like liquid nitrogen. The cabinet body 10 is provided with a plurality of circulating fans 12 with vanes 121 located within cabinet body 10 to form a downward blowing air flow so that air within cabinet body 10 can circulate sufficiently. The temperature of the test specimen test zone can quickly rise and fall and achieve a uniform degree.

Based on the above construction, cabinet body 10 can match a two-stage type control system (such as a control system by JC Systems Co.) to perform control of all heating (all electric heating tubes 13 on for heating)3 all cooling with all liquid nitrogen cryogenic valves 153, 163 on), and constant temperature micro-adjustment (with only one group of electric heating tubes 13 or liquid nitrogen cryogenic valve 153, 163 on) so as to achieve quick temperature rise or fall and quick temperature stability when temperature is constant, for performing high change rate of temperature test.

Figure 5:
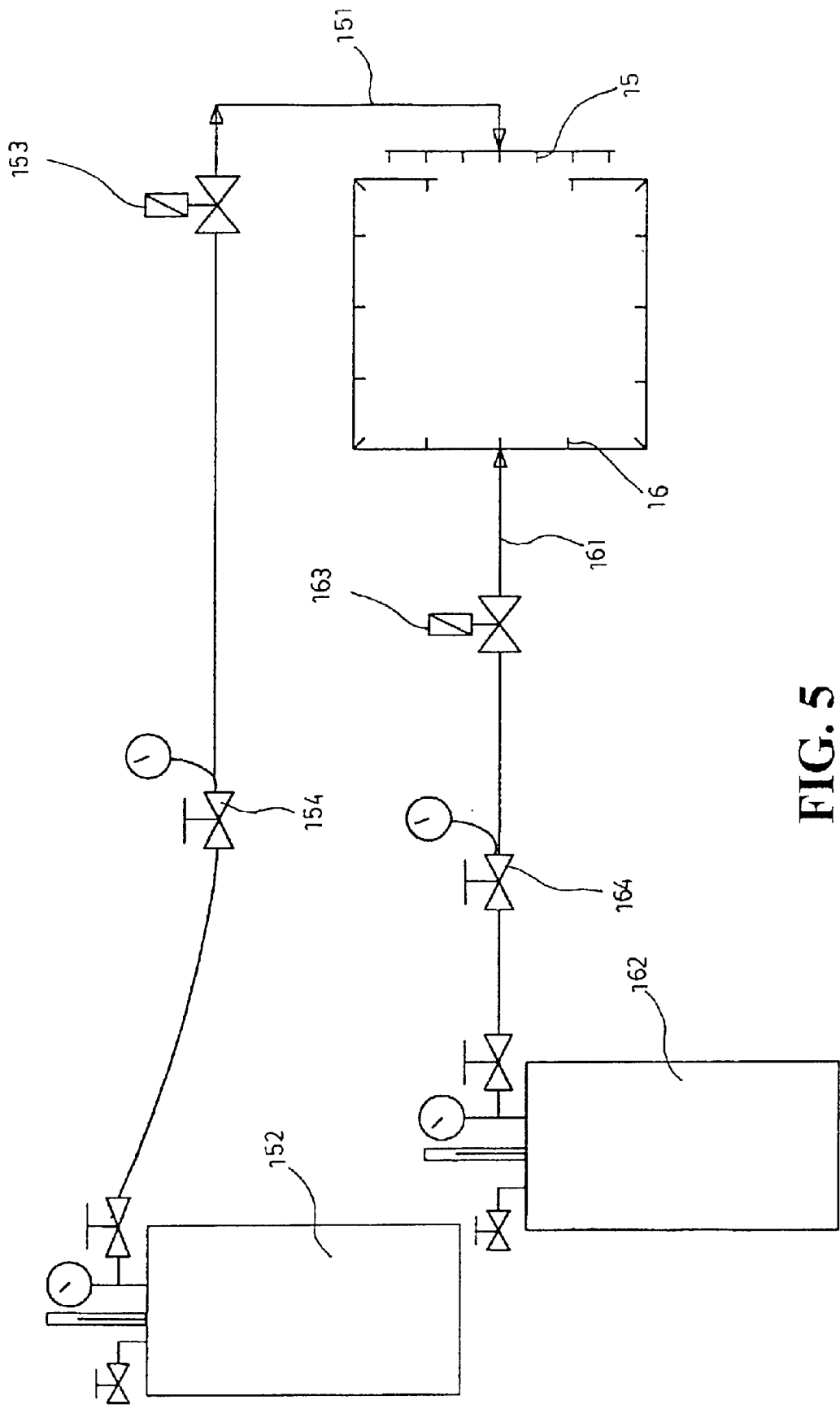
FIG. 5 is a schematic view of liquid nitrogen pipes of this invention.
Figure 6:
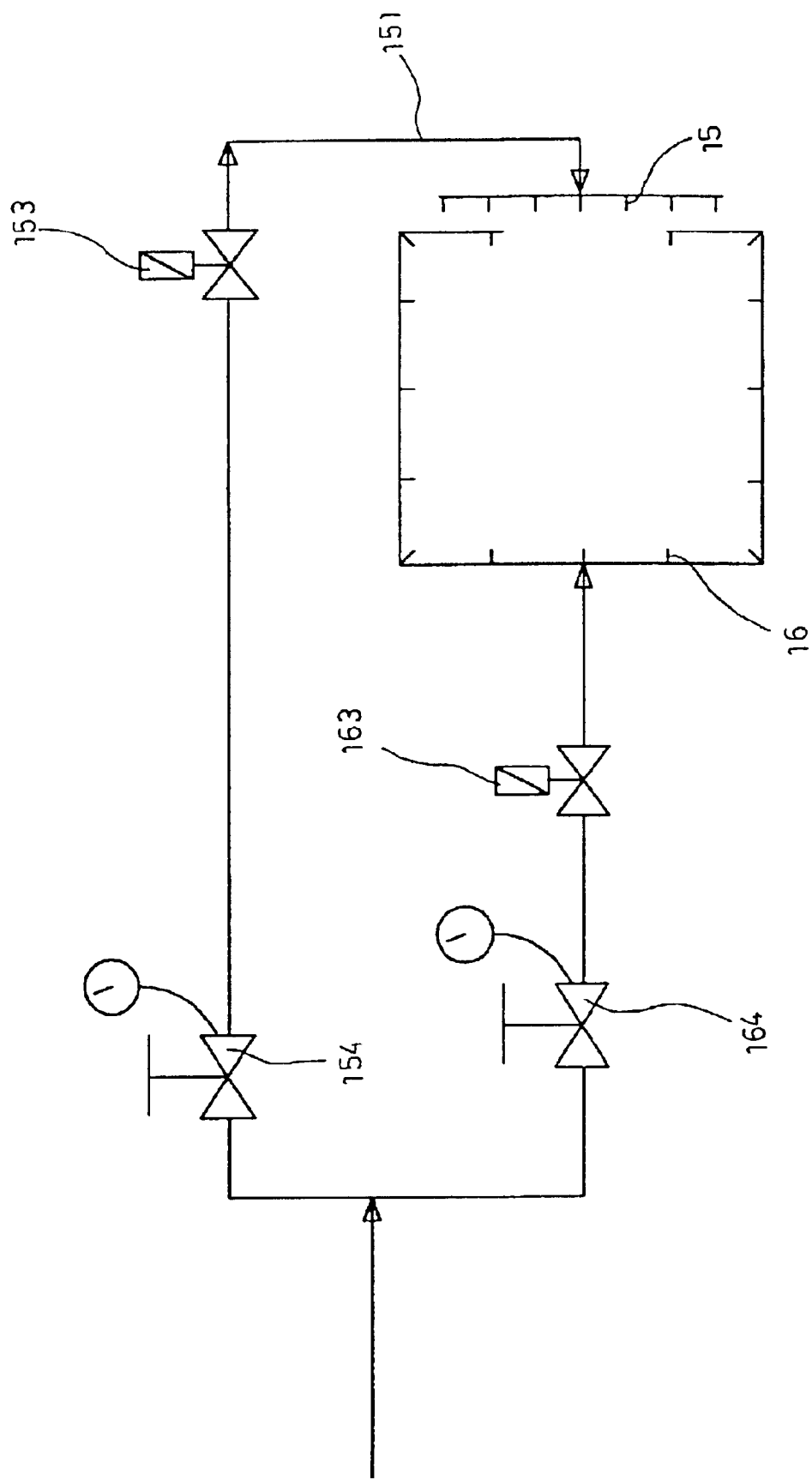
FIG. 6 is a schematic view of another form of liquid nitrogen pipes of this invention.

Referring to FIG. 5, liquid nitrogen pipes 151, 161 of nozzles 15, 16 may be connected to Dewars liquid nitrogen bottles 152, 162, or pipes 151, 161 are connected to the same liquid nitrogen supply source (larger pipe diameter) (see FIG. 6). The entire liquid nitrogen pipes are surrounded by thermal insulating sleeves. Pipes 151, 161 are provided with pressure adjusting valves (including pressure meters) 154, 164 to adjust suitable liquid nitrogen pressure. Pressure adjusting pressure valves 154, 164 and cryogenic valves 153, 163 are connected by flexible stainless steel hose, with outlet ends connected to nozzle sets within the cabinet. The length of pipes between cryogenic valves 153, 163 and nozzle sets are preferably as short as possible to prevent delay in low temperature control due to large amounts of gas resulting from evaporation of liquid nitrogen within the pipes. Therefore, cryogenic valves are secured on the outside of the cabinet body to timely and automatically supply liquid nitrogen to nozzle sets 15,16 to spray mist-like liquid nitrogen, achieving good low temperature control. During a high cooling rate temperature drop in cabinet 10, nozzle sets 15, 16 can simultaneously eject liquid nitrogen. At a constant low temperature, only liquid nitrogen pipe 151 is used for input. The other pipes are automatically closed to thereby achieve precise micro-adjustment. Hence, quick temperature reduction and stability can be achieved.

Figure 7:
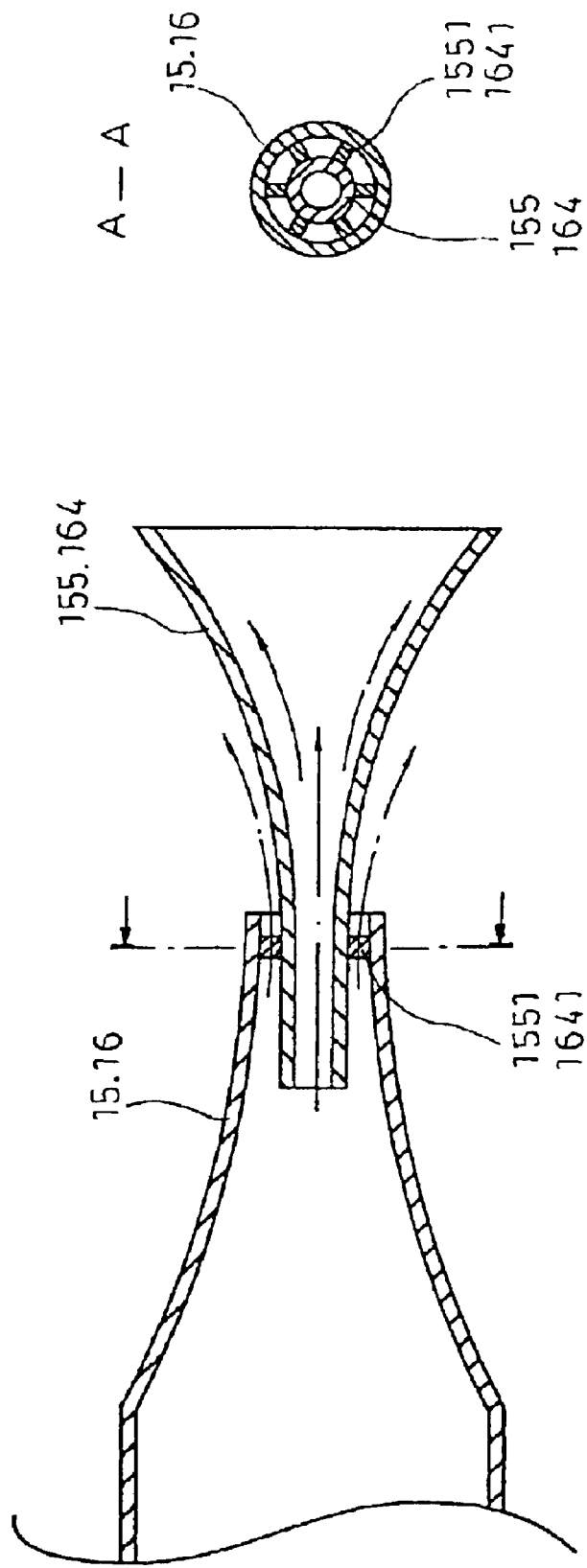
FIG. 7 is a schematic view of the structure of nozzles of this invention.

Referring to FIG. 7, outlets of nozzles 15, 16 are provided with flared tube sleeves 155, 164. Nozzles 15, 16 and flared tube sleeves 155, 164 are connected by several points 1551, 1641 by soldering. By forming several small holes between nozzles 15, 16 and flared tube sleeves 155, 164 to enable liquid nitrogen to eject therefrom quickly for dispersion and evaporation as gas, the liquid nitrogen is prevented from being ejected in jets or drops directly toward the test space or onto the test specimens.

Figure 8:
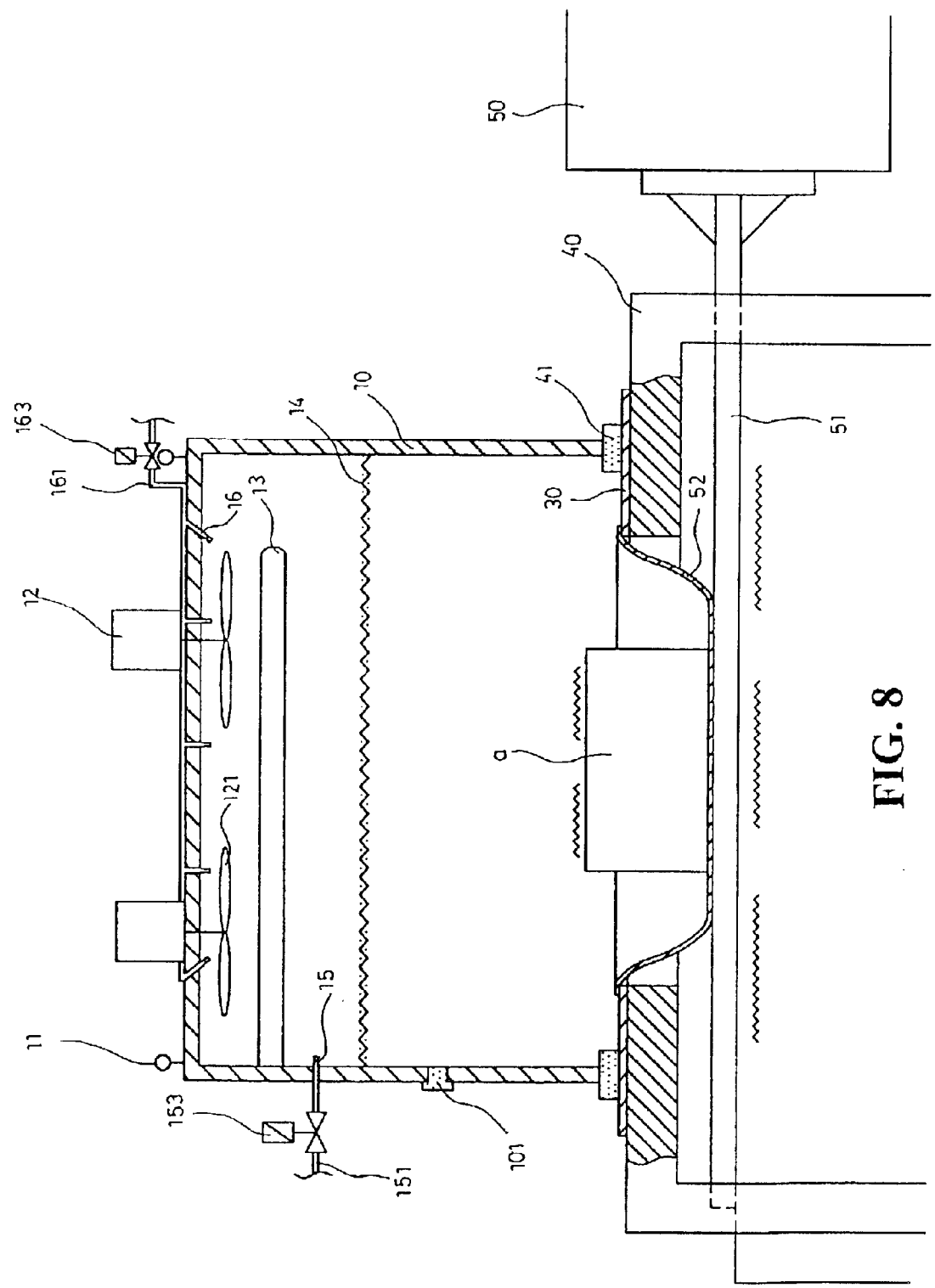
FIG. 8 a schematic view of the invention when used with a slip table of shaker.

Referring to FIG. 8, cabinet body 10 can be used alone to carry out high transition rate of temperature test and for ordinary temperature cabinet uses. Bottom portions of four side walls of the cabinet body are mounted with beat insulating sponges 41, with the weight of cabinet body 10 pressing heat insulating sponges 41 and placed on bakelite baseplate 30 with an opening. The bakelite baseplate 30 is placed on a support seat 40. A level slide table 51 extending from level, axial shaker 50 is located below support seat 40. The periphery of bakelite baseplate 30 with opening is provided with heat-resistant thin soft rubber 52 to provide a heat insulating function. The test specimen with fixture is fixed on the slip table 51 through heat-resistant thin soft rubber 52. By means of the above construction, cabinet body 10 can carry Out temperature/vibration X,Y axial test.

Figure 9:
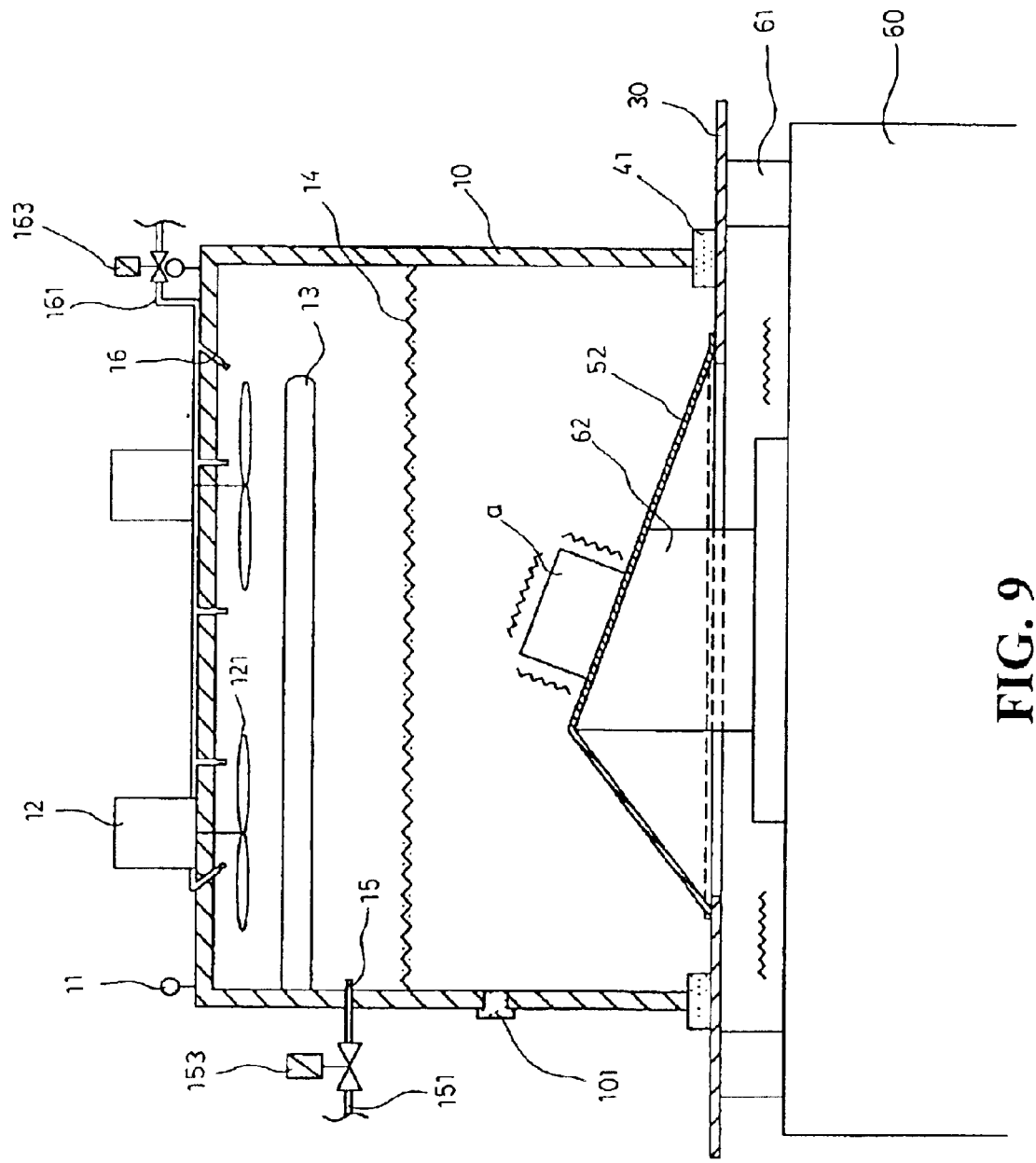
FIG. 9 is a schematic view of the invention when used with a vertical type shaker.

Referring to FIG. 9, cabinet body 10 of this invention may also be set up with a vertical type shaker 60. Structurally, cabinet body 10 is placed on bakelite baseplate 30 with opening. Bakelite baseplate 30 is placed on a plurality of support blocks 61 (metal blocks or wooden blocks) disposed on the body of a vertical type vibrating machine adjacent to the armature. A test specimen with fixture is fixed to an extension table 62 of the shaker 60 via a heat-resistant thin soft rubber 52 for conducting vertical axial temperature/vibration tests.

Figure 10:
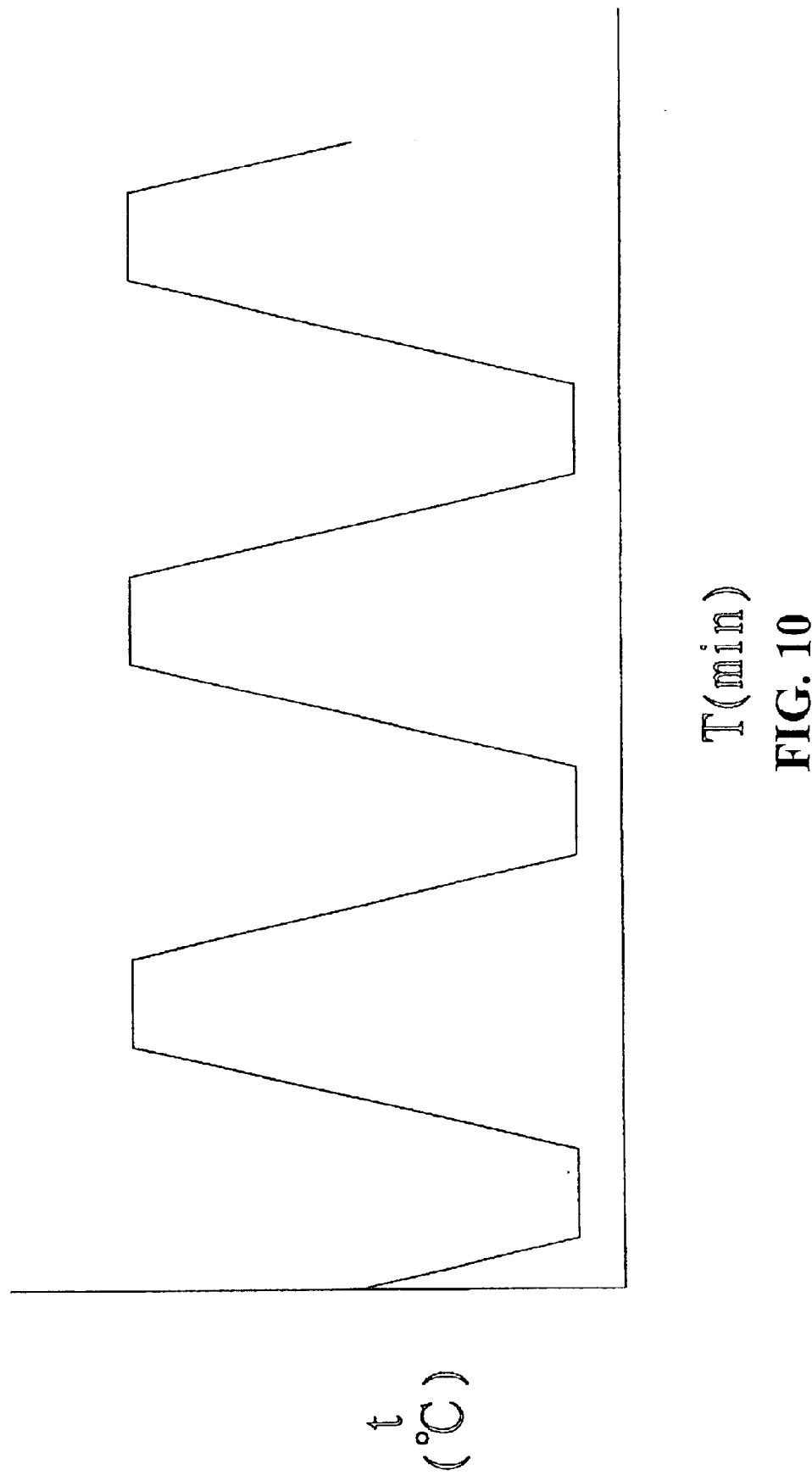
FIG. 10 is a temperature time curve graph of a high variable rate temperature test according to this invention.

Referring to FIG. 10, the high thermal change rate temperature test conducted in this invention can satisfy test requirements of at least 40° C. per minute temperature change rate, and when the required high or low temperature is reached, the temperature can be kept stable.

In conclusion, the high thermal change rate test devices of this invention, in conjunction with test forms, has great assembly flexibility, high mobility, and multiple test uses, and can quickly heat up or cool down temperature and permit constant temperature micro-adjustment to bring temperature quickly to a stable state. The dispersion of spray ejected from liquid nitrogen nobles has a satisfactory effect. The invention thus can completely eliminate the drawbacks of conventional temperature/vibration cabinets.

Although the present invention has been illustrated and described with reference to the preferred embodiment thereof, it should be understood that it is in no way limited to the details of such embodiment but is capable of numerous modifications within the scope of the appended claims.

What is claimed is:

1. A high thermal change rate temperature test device which is provided with a cabinet body with each peripheral side made from heat insulating cabinet walls, and a bottom portion matching a baseplate of different test forms, the baseplate being made from a light and easy to assemble material of low heat conductivity comprising bakelite; bottom portions of four side walls of the cabinet body having soft thermal insulating sponges attached thereto so that when covering the bakelite baseplate, the weight of the cabinet body itself can press the thermal insulating sponges to form internal and external heat insulation for the cabinet body; an upper end of the cabinet body being provided with a plurality of circulation fans; an upper end of the interior of the cabinet body being provided with high speed electric heating tubes, inner wall surfaces of the upper end of the interior of the cabinet body being provided with a plurality of nozzles connected to liquid nitrogen pipes, the liquid nitrogen pipes being provided with pressure adjusting valves, pressure meters, cryogenic valves, the pressure adjusting valves and the cryogenic valves being connected by flexible stainless steel hose, outlet ends of the cryogenic valves for controlling liquid nitrogen being connected to the nozzles in the cabinet, the cryogenic valves and nozzle sets being connected by short pipes to prevent delay in low temperature control; the liquid nitrogen pipes being designed to be multiple in number, each being connected to a Dewars liquid nitrogen bottle, the cryogenic valves of all pipes being simultaneously opened during full-speed temperature cooling to eject liquid nitrogen, the cryogenic valve of only one group of the liquid nitrogen pipes being used at a constant temperature, and a minority of the nozzles being subjected to temperature micro-adjustment, achieving a satisfactory temperature controlling effect of quick temperature cooling and quick stability of temperature when temperature is constant.

2. The high thermal change rate temperature test device as claimed in claim 1, wherein an outlet end of the liquid nitrogen nozzle has a flared tube sleeve mounted thereon, the nozzle and the flared tube sleeve being connected by solder points to form a plurality of small holes between the nozzle and the flared tube sleeve.

3. The high variable rate temperature test apparatus as claimed in claim 1, wherein the cryogenic valve of each liquid nitrogen pipe has a pressure adjusting valve and a pressure meter mounted in front thereof to adjust suitable liquid nitrogen pressure so that adequate liquid nitrogen can flow into the cabinet to reach the required temperature cooling rate and does not exceed the pressure tolerable by the cryogenic valve, and prevent excessively low temperature.

4. The high thermal change rate temperature test apparatus as claimed in claim 1, wherein the interior of the cabinet body is provided with a stainless steel mesh that is convenient to remove.

5. The high thermal change rate temperature test apparatus as claimed in claim 1, wherein the bakelite baseplate matching the cabinet body is centrally provided with an opening.

6. The high thermal change rate temperature test apparatus as claimed in claim 5, wherein the central opening of the bakelite baseplate has a periphery provided with a heat-resistant thin soft rubber.

7. The high thermal change rate temperature test apparatus as claimed in claim 1, wherein the bottom portion of the cabinet body matching the bakelite base plate with opening is placed on a support seat, a level slide table is located below the bakelite baseplate and the thin soft rubber so that test specimen with fixture is fixed on the slip table via the thin soft rubber before placement of the cabinet body.

8. The high thermal change rate temperature test apparatus as claimed in claim 1, wherein the bakelite baseplate with opening is placed on support blocks on the body of a vertical type shaker adjacent to an armature so that test specimen with fixture is locked on the armature or the extension table of the shaker via the heat-resistant thin soft rubber before placement of the cabinet body.

9. The high thermal change rate temperature test apparatus as claimed in claim 8, wherein the periphery of the central opening of the bakelite baseplate is provided with heat-resistant thin soft rubber covering the extension table and the armature of the vertical type shaker below.

10. The high thermal change rate temperature test apparatus as claimed in claim 1, wherein the liquid nitrogen pipe is connected to a single tube supply source of a liquid nitrogen storage tank via a manifold.

* * * * *